(12) United States Patent
Dams et al.

(10) Patent No.: US 8,844,386 B2
(45) Date of Patent: Sep. 30, 2014

(54) METHOD AND APPARATUS FOR ANALYZING SAMPLES OF METAL MELTS

(75) Inventors: Francis Dams, Kessel-Lo (BE); Lihuan Song, Lommel (BE); Johan Knevels, Bree (BE); Gerrit Broekmans, Paal (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 280 days.

(21) Appl. No.: 13/310,960

(22) Filed: Dec. 5, 2011

(65) Prior Publication Data

US 2012/0137757 A1 Jun. 7, 2012

(30) Foreign Application Priority Data

Dec. 7, 2010 (DE) .......................... 10 2010 053 710

(51) Int. Cl.
| | |
|---|---|
| *G01N 33/20* | (2006.01) |
| *G01N 1/12* | (2006.01) |
| *C21C 5/46* | (2006.01) |
| *F27D 21/00* | (2006.01) |
| *F27D 19/00* | (2006.01) |
| *C21C 5/52* | (2006.01) |

(52) U.S. Cl.
CPC ...... *G01N 33/206* (2013.01); *F27D 2019/0006* (2013.01); *C21C 5/4673* (2013.01); *G01N 1/125* (2013.01); *F27D 19/00* (2013.01); *F27D 21/00* (2013.01); *C21C 2005/5288* (2013.01)
USPC ................... 73/864.81; 73/863.81; 73/864.51; 73/864.83

(58) Field of Classification Search
USPC ........ 73/863.81, 864, 864.51, 864.81–864.91
See application file for complete search history.

(56) References Cited

U.S. PATENT DOCUMENTS

| | | | | |
|---|---|---|---|---|
| 3,353,808 | A * | 11/1967 | Norburn ......................... 239/589 |
| 3,457,790 | A * | 7/1969 | Hackett ....................... 73/864.56 |
| 3,460,393 | A * | 8/1969 | Putnam ........................ 73/863.11 |
| 3,490,289 | A | 1/1970 | Mangin |
| 3,521,959 | A * | 7/1970 | Fassel et al. ................... 356/316 |
| 3,534,614 | A * | 10/1970 | Creswell .................... 73/864.52 |
| 3,638,500 | A * | 2/1972 | Wetzel ........................ 73/863.31 |
| 3,646,816 | A * | 3/1972 | Hance et al. ............... 73/864.56 |

(Continued)

FOREIGN PATENT DOCUMENTS

| | | |
|---|---|---|
| DE | 1773164 A1 | 12/1971 |
| DE | 2206590 A1 | 8/1972 |

(Continued)

OTHER PUBLICATIONS

Search Report issued Dec. 10, 2012 in BE Application No. 201100282.

(Continued)

*Primary Examiner* — David A Rogers
(74) *Attorney, Agent, or Firm* — Panitch Schwarze Belisario & Nadel LLP

(57) ABSTRACT

A method is provided for analyzing samples of metal melts, wherein a sample is taken from a metal melt using a sampler having a sample chamber and which is constructed as an immersion lance. The method includes transporting the sample from the sampler through a transport conduit to the sphere of action of an analytical device, and analyzing the sample there using the analytical device.

12 Claims, 4 Drawing Sheets

(56) References Cited

U.S. PATENT DOCUMENTS

| | | | | |
|---|---|---|---|---|
| 3,672,774 | A | * | 6/1972 | Bojic et al. ............... 356/313 |
| 3,709,040 | A | * | 1/1973 | Coe .............................. 374/26 |
| 3,717,034 | A | * | 2/1973 | Dukelow et al. ............ 374/140 |
| 3,974,698 | A | * | 8/1976 | Scott, Jr. .................... 73/864.54 |
| 4,120,204 | A | * | 10/1978 | Cure ........................... 73/864.57 |
| 4,197,745 | A | * | 4/1980 | Kumbrant .................. 73/864.53 |
| 4,206,652 | A | * | 6/1980 | Kumbrant .................. 73/864.55 |
| 4,211,117 | A | * | 7/1980 | Cure ........................... 73/864.55 |
| 4,326,426 | A | * | 4/1982 | Falk ............................ 73/864.59 |
| 4,342,633 | A | | 8/1982 | Cure |
| 4,428,245 | A | * | 1/1984 | Nakamura et al. ......... 73/864.52 |
| 4,489,604 | A | * | 12/1984 | Kumbrant et al. ........... 73/432.1 |
| 4,499,777 | A | * | 2/1985 | Hackett ...................... 73/864.56 |
| 4,503,716 | A | * | 3/1985 | Wuensch .................... 73/864.57 |
| 4,538,794 | A | * | 9/1985 | Scherff ........................... 266/79 |
| 4,699,014 | A | * | 10/1987 | Boron ......................... 73/864.57 |
| 4,848,438 | A | * | 7/1989 | Gray ............................... 164/4.1 |
| 4,932,271 | A | * | 6/1990 | Haughton .................... 73/864.53 |
| 4,941,364 | A | * | 7/1990 | Haughton .................... 73/864.53 |
| 4,998,432 | A | | 3/1991 | Plessers et al. |
| 5,060,530 | A | * | 10/1991 | Haughton .................... 73/864.53 |
| 5,156,799 | A | * | 10/1992 | Baerts ............................. 266/79 |
| 5,187,991 | A | * | 2/1993 | Baerts ........................ 73/864.56 |
| 5,415,052 | A | * | 5/1995 | Baerts ........................ 73/864.55 |
| 5,515,739 | A | * | 5/1996 | Baerts ........................ 73/864.55 |
| 5,614,682 | A | * | 3/1997 | Baerts ........................ 73/864.58 |
| 5,675,097 | A | * | 10/1997 | Donnelly et al. ............ 73/864.59 |
| 5,979,253 | A | * | 11/1999 | Knevels et al. ............. 73/864.58 |
| 6,433,862 | B1 | | 8/2002 | Schock et al. |
| 7,365,841 | B2 | | 4/2008 | Plessers et al. |
| 7,370,544 | B2 | * | 5/2008 | Neyens et al. ............. 73/864.59 |
| 2005/0279183 | A1 | * | 12/2005 | Neyens et al. ................. 73/866 |
| 2011/0308319 | A1 | * | 12/2011 | Neyens et al. ................. 73/700 |
| 2012/0082183 | A1 | * | 4/2012 | Beyens ........................ 374/179 |

FOREIGN PATENT DOCUMENTS

| | | | |
|---|---|---|---|
| DE | 3033786 A1 | 4/1982 | |
| DE | 3103695 A1 | 8/1982 | |
| DE | 3200010 A1 * | 7/1983 | ............... C21C 5/30 |
| DE | 3311360 A1 | 10/1984 | |
| DE | 3344944 A1 | 6/1985 | |
| EP | 0307430 B1 | 1/1992 | |
| EP | 0563447 A1 | 10/1993 | |
| GB | 1555309 A | 11/1979 | |
| JP | 55-134122 A | 10/1980 | |
| JP | 03-071057 A | 3/1991 | |
| JP | 06222194 A1 * | 8/1994 | |
| SU | 1381359 A1 * | 3/1988 | |
| WO | 2005059527 A1 | 6/2005 | |

OTHER PUBLICATIONS

Office Action issued Apr. 13, 2012 in DE Application No. 10 2010 053 710.1.

Office Action issued Mar. 17, 2011 in DE Application No. 102010053710.1.

* cited by examiner

METHOD AND APPARATUS FOR ANALYZING SAMPLES OF METAL MELTS

BACKGROUND OF THE INVENTION

The invention relates to a method for analyzing samples of metal melts, wherein a sample is taken from a metal melt using a sampler having a sample chamber and which is constructed as an immersion lance. Further, the invention relates to a device for taking samples in metal melts, using a sampler having a sample chamber and which is constructed as an immersion lance, wherein the device may be particularly suitable for carrying out the method according to the invention.

In molten metal processes, particularly in the manufacture of cast iron or steel, regular analyses of the melt are necessary. For the economy of the process it is necessary thereby that the analyses can be carried out in the shortest possible time, in order to be able to regulate process guidance accordingly in a timely manner.

Sample analysis methods are known, for example, from European Patent EP 563 447 B1. Using the technique described there, the nitrogen content in metal melts can be determined. Similar devices and methods are known from European Patent EP 307 430 B1. Using the device described there, in particular, the hydrogen content in metal melts can be analyzed. International Patent Application Publication WO 2005/059527 A1 discloses analytical methods and devices for the metal melt, which work with single-use spectrometers. From U.S. Pat. No. 4,342,633 immersion probes for single use are known, with which temperature and oxygen content of metal melts can be determined. In Japanese patent application publication (Kokai) JP 3-071057 A a sampling device for steel melts is described, in which the sample is taken with the aid of an immersion lance, wherein the sample during withdrawal of the lance from the metal melt is brought into a hermetically sealed chamber. From German published patent application DE 33 44 944 A1 it is known to take samples, to transport them to analytical laboratories and to conduct the analysis there. Furthermore, a spectroscopic investigation of metallurgical immersion probes is known from German published patent application DE 32 00 010 A1. Here, in particular, the sample is maintained under vacuum or inert gas atmosphere, in order to prevent oxidation of the hot sample.

BRIEF SUMMARY OF THE INVENTION

An object of the present invention is to shorten further the time between sample collection and analysis and thereby to avoid adulteration of the sample.

The object is achieved by the method according to the invention for analyzing samples of metal melts, particularly of cast iron or steel melts, in which a sample is taken from a metal melt using a sampler having a sample chamber and which is constructed as an immersion lance. The method is characterized in that the sample from the sampler is transported through a transport conduit to the sphere of action of an analytical device and in that the sample is analyzed there by the analytical device. In particular, the analytical device may be a spectrometer.

Here, the sample is moved directly from the immersion lance into the transport conduit (directly following the immersion lance) and from there to the analytical device, so that first a rapid transport is guaranteed, and second, external influences on the sample are largely excluded. The transport conduit may be constructed as a pneumatic tube line. Preferably, the sample can be divided into several (for example 2 to 4) solid parts, wherein the division may already take place in the sampler and parts of the sample may be transported to the sphere of action of the analytical device.

Preferably, the sample may also be connected to a portion of the sample chamber which is detachable from the complete sample chamber and, together with this portion, may be transported to the sphere of action of the analytical device. It may also be advantageous that the sample together with the sample chamber is transported through the transport conduit to the sphere of action of the analytical device, where a portion of the sample chamber is removed and the thus-exposed surface area of the sample is analyzed.

In particular, it may be suitable that during the transport through the transport conduit the sample is exposed to vacuum or inert gas. It may also be advantageous that vacuum or inert gas is generated prior to sampling, at least in the sample chamber. It may also be suitable that vacuum or inert gas is generated at least in the sample chamber and maintained until the sample is cooled to a temperature of ≤400° C. The transport of the sample may be carried out preferably by compressed gas. A transport under vacuum (suction of the sample) is also possible. As the compressed gas, in particular, an inert gas (for example argon) may be used, which optionally may be replaced with compressed air, when the sample has cooled to a temperature of ≤400° C.

The device according to the invention for taking samples in metal melts, using a sampler having a sample chamber and which is constructed as an immersion lance, is characterized in that the sample chamber is arranged in a cartridge, such that the sampler is connected to a first end of a transport conduit of the cartridge containing the sample or the sample-containing sample chamber, and in that a second end of the transport conduit is connected to an analytical device. The outer contour of the cartridge is adapted to the inner contour of the immersion lance and to the immediately following transport conduit and serves for the transport of the sample chamber. The cartridge may be integrated into the sample chamber, for example, when the outer contour of the sample chamber is adapted to the inner contour of the immersion lance and transport conduit. In particular, the analytical device may be a spectrometer.

Expediently, the sample chamber or a portion thereof is detachable from the sampler and is transportable through the transport conduit. Furthermore, it is advantageous that the transport conduit have a compressed gas connection and/or a vacuum connection. Furthermore, it is expedient that the sample chamber and/or the cartridge have a vacuum connection or an inert gas connection. Using the device according to the invention, a quick sampling and transporting of the sample to an analytical device is possible, without the sample being exposed to damaging environmental impacts in between.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
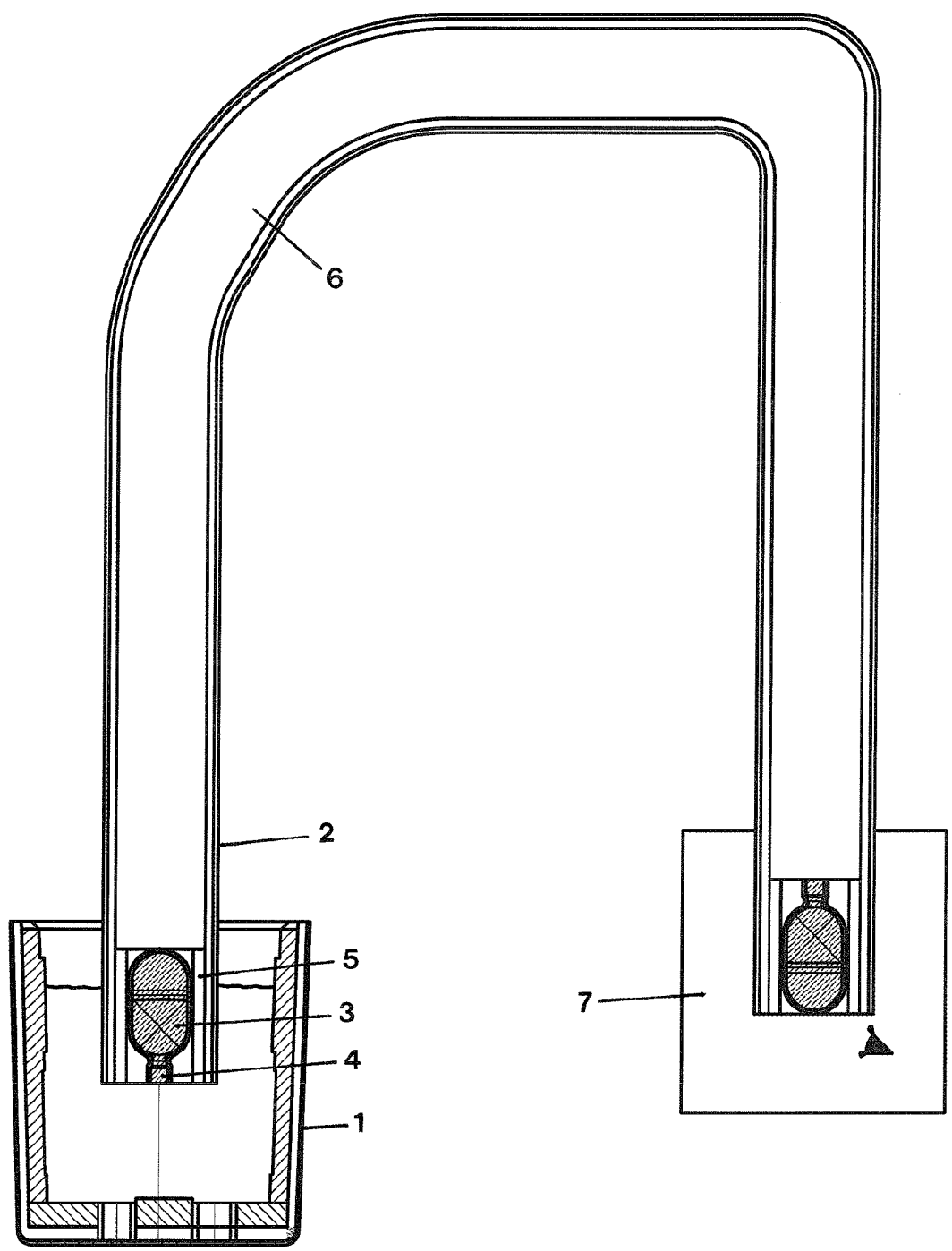
FIG. 1 is a schematic, side, sectional representation of a sampling and measuring arrangement according to an embodiment of the invention.

In FIG. 1 a melt container 1 for molten steel is represented, in which an immersion lance 2, serving as a sampler, is immersed. A sample chamber 3 is arranged at the immersion end of the immersion lance. The sample chamber 3 is a so-called lollipop sample chamber, thus a flat sample chamber having an elliptical cross section, which has an inlet 4 at its immersion end. The sample chamber 3 is fixed in a cartridge 5. Using this cartridge 5, the sample chamber 3 is transported by the immersion lance 2 and the directly following transport conduit 6 to a spectrometer 7, which serves as an analytical device.

Figure 2:
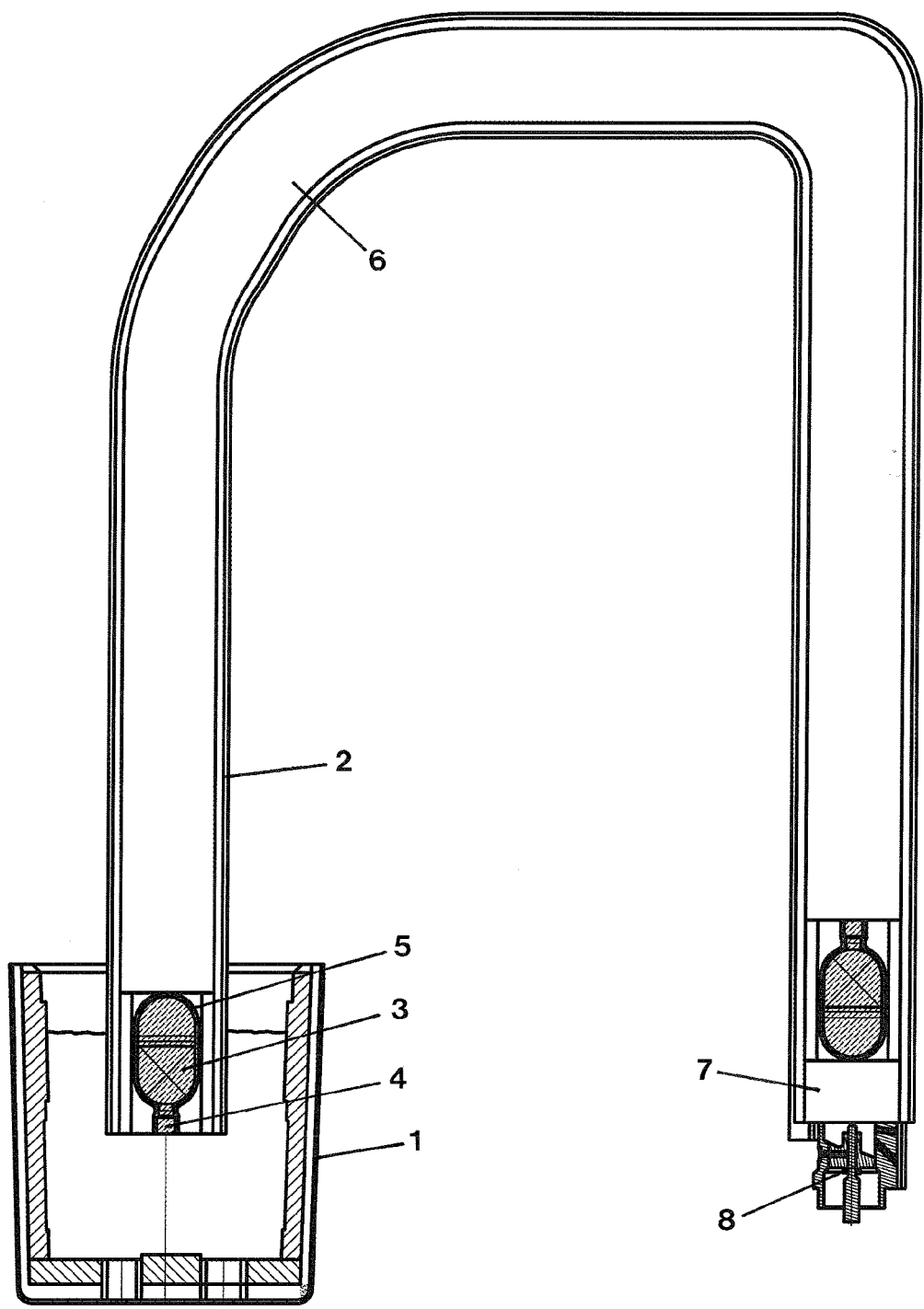
FIG. 2 is a similar representation of a sampling and measuring arrangement according to another embodiment of the invention.

In FIG. 2 a very similar arrangement is represented, wherein the spectrometer 7 is shown with its spark stand 8. In the arrangements shown in the figures, the sample chamber 3 is opened after its arrival at the spectrometer 7. Here, the inert gas introduced into the sample chamber 3 evaporates before immersion into the molten steel.

The inert gas supply to sample chamber 3 is carried out in a known manner, as shown for example in DE 32 00 010 A1. Using inert gas, which alternatively may be replaced by vacuum, prevents the liquid steel sample or the cooled steel sample from oxidizing at high temperatures.

Upon reaching the spectrometer 7, the sample has a temperature of well below 400° C., so that inert gas or vacuum to protect the sample is no longer needed. Sample chamber 3 opens upon arrival at spectrometer 7. The opening can occur, among other ways, by the kinetic force of the sample, but also mechanically by opening the two half shells of the sample chamber 3 by a spring or by a manipulator, for example by a cutting disk or even by action of compressed air. By detaching at least one of the two half shells of the sample chamber 3, a surface of the sample becomes accessible for analysis. Since the sample collection and the transportation of the sample is carried out under inert gas (for example argon), oxidation is prevented, so that the sample for analysis does not additionally have to be freed of oxidation in an appropriate way, hence sample preparation prior to analysis is no longer necessary.

Such a sample feed to an analytical device takes place very quickly and directly, without intermediate stages during which the sample has to be transported on a different transport path. By connection of the transport conduit 6 with the immersion lance 2 and the analytical device, the use of an elaborate analytical device in the immediate vicinity of the melt is redundant. In practice, the analysis can be carried out in less than two minutes, because the transport is very fast and begins immediately after sampling. In addition, an automatic sample identification is possible, by which the process analysis can be improved. The analytical device may be installed in a mobile laboratory or in an otherwise fixed laboratory, for example in a central laboratory. In steel mills such laboratories are sufficiently available.

In the Figures the sample chamber 3 is shown as a flat sample chamber, which is fixed in a cartridge 5. The immersion lance 2 has a round internal cross-section, which connects seamlessly to the likewise round and equal size internal cross-section of the transport conduit 6, so that the cartridge 5 with its likewise round exterior cross-section can be transported without any problems.

Instead of a flat sample chamber, it is also conceivable that a sample chamber having a round cross section (perpendicular to the direction of transport) is used. In this case, the cartridge is essentially the same as the outer shell of the sample chamber 3, so that the cartridge is integrated directly into the sample chamber 3.

Figure 3:
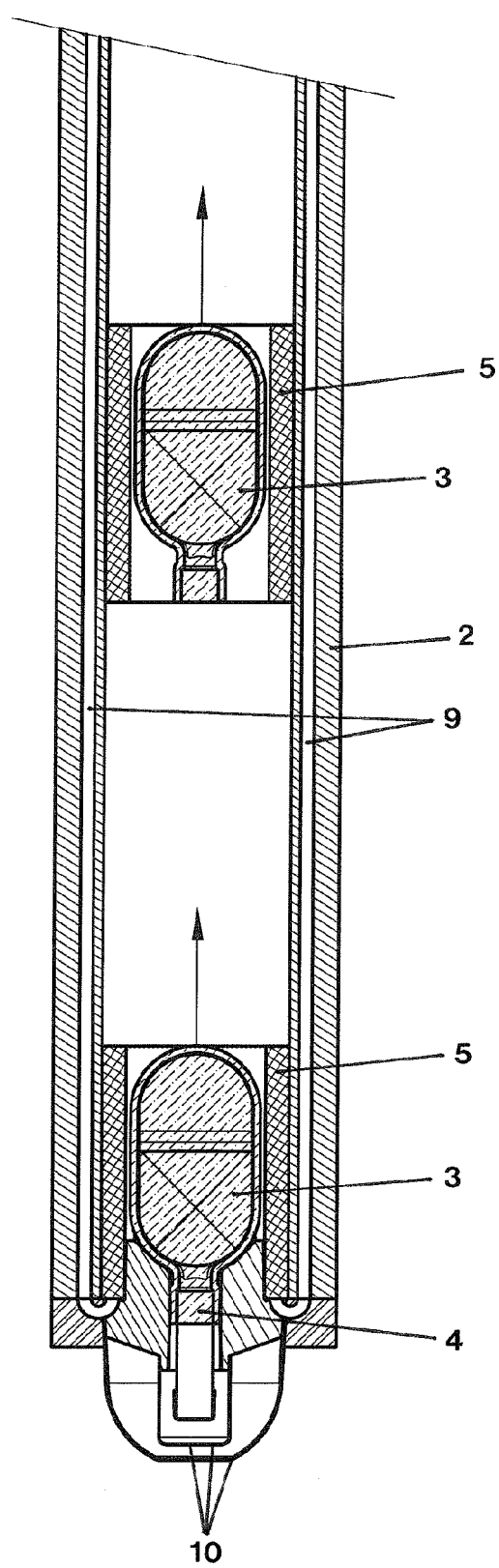
FIG. 3 is a partial, schematic, sectional representation showing a sampler and the transport of a sample according to an embodiment of the invention.

The transport of the sample chamber 3 to the analytical device, which, for example, comprises the above-mentioned spectrometer 7, takes place by compressed air. This is shown in FIG. 3 in two phases of motion of the sample chamber 3. At its end, not shown in FIG. 3, the immersion lance 2 transitions seamlessly into the transport conduit 6. Within the wall of the immersion lance 2 and optionally the transport conduit 6, compressed gas lines are arranged, with whose aid a gas may be pressed with sufficiently high pressure against the immersion end of the cartridge 5, so that it is transported in the direction of the analytical device.

The cross section of the cartridge 5 that remains free can suitably be closed using a disc made of a refractory material, for example at the end of the cartridge 5 away from the immersion end, so that the gas pressure effectively causes the transport of the sample chamber 3. In the immersion position of the sample chamber 3, in FIG. 3 the protective caps 10 arranged at the inlet opening 4 of the sample chamber 3 are shown, which caps melt or dissolve when immersed in the steel melt, so that the steel melt may flow into the sample chamber 3.

Figure 4:
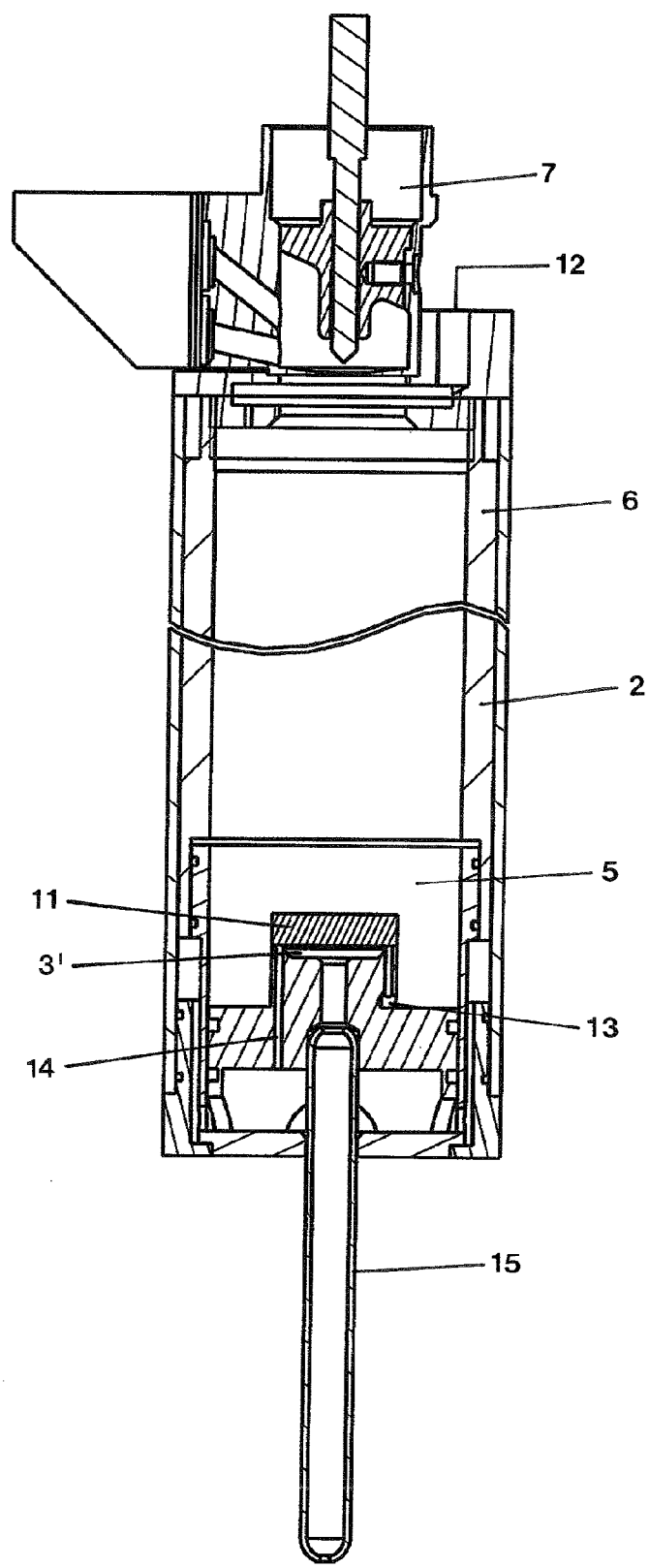
FIG. 4 is a schematic, side, sectional representation of another embodiment of a sampler according to the invention.

FIG. 4 shows another possible embodiment of the invention. The lower part of FIG. 4 shows the immersion lance 2, and the upper part of FIG. 4 shows the transport conduit 6 leading into the analytical device. The sample chamber 3' is constructed as a flat sample chamber, whose larger extension runs perpendicular to the immersion direction. At its end facing away from the immersion end, the sample chamber 3' is equipped with a removable lid 11, which is removed after arrival of the sample chamber 3' at the spectrometer 7. The spectrometer 7 contains a spark stand, with whose aid the sample will be analyzed at its freely accessible surface after removal of the lid 11.

The analytical device contains a gas inlet 12. A gas conduit 13 is provided for the introduction of the inert gas—compressed gas in the immersion lance 2 at its immersion end. There, a gas supply line 14 for the introduction of inert gas into the sample chamber is also arranged. The sample chamber itself is filled through an inlet pipe 15 made of quartz glass.

The individual parts of the device are constructed of materials conventionally used in samplers.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for analyzing samples of metal melts, the method comprising taking a sample from a metal melt using a sampler having a sample chamber and constructed as an immersion lance, transporting the sample from the sampler through a transport conduit directly following the immersion lance to an analytical device, and analyzing the sample by the analytical device.

2. The method according to claim 1, wherein the analytical device comprises a spectrometer.

3. The method according to claim 1, wherein the transporting of the sample through the transport conduit occurs with action of vacuum or inert gas on the sample.

4. The method according to claim 3, wherein the vacuum or inert gas is generated at least in the sample chamber already before the taking of a sample.

5. The method according to claim 3, wherein the vacuum or inert gas is generated at least in the sample chamber and is maintained until the sample is cooled to a temperature of not more than 400° C.

6. The method according to claim 1, wherein the transporting of the sample takes place by compressed gas.

7. The method according to claim 6, wherein the compressed gas comprises an inert gas, optionally replaced by compressed air when the sample has cooled to a temperature of not more than 400° C.

8. A device for taking samples in metal melts, the device comprising a sampler having a sample chamber and being constructed as an immersion lance, the sample chamber being arranged in a cartridge, the sampler being connected to a first end of a conduit for transporting the cartridge containing the sample or for transporting the sample-containing sample chamber, and a second end of the transport conduit being connected to an analytical device, wherein the transport conduit is arranged to directly follow the immersion lance.

9. The device according to claim 8, wherein the analytical device is a spectrometer.

10. The device according to claim 8, wherein the sample chamber or a portion thereof is detachable from the sampler and transportable through the transport conduit.

11. The device according to claim 8, wherein the transport conduit has at least one of a compressed gas connection and a vacuum connection.

12. The device according to claim 8, wherein the sample chamber or the cartridge has a vacuum connection or an inert gas connection.

* * * * *